US011404142B2

(12) United States Patent
Stuelpnagel et al.

(10) Patent No.: US 11,404,142 B2
(45) Date of Patent: Aug. 2, 2022

(54) PROCESSES FOR CALCULATING PHASED FETAL GENOMIC SEQUENCES

(71) Applicant: Ariosa Diagnostics, Inc., San José, CA (US)

(72) Inventors: John Stuelpnagel, San Jose, CA (US); Craig Struble, San Jose, CA (US); Eric Wang, San Jose, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 525 days.

(21) Appl. No.: 16/410,878

(22) Filed: May 13, 2019

(65) Prior Publication Data

US 2019/0378593 A1 Dec. 12, 2019

Related U.S. Application Data

(63) Continuation of application No. 13/898,239, filed on May 20, 2013, now Pat. No. 10,289,800.

(60) Provisional application No. 61/649,445, filed on May 21, 2012.

(51) Int. Cl.
*G16B 20/20* (2019.01)
*G16B 20/00* (2019.01)

(52) U.S. Cl.
CPC ............ *G16B 20/20* (2019.02); *G16B 20/00* (2019.02)

(58) Field of Classification Search
CPC ........ G16B 50/00; G16B 20/20; G16B 40/00; G16B 20/00
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,136,229 A | 10/2000 | Cui et al. |
| 6,141,096 A | 10/2000 | Stern et al. |
| 6,156,504 A | 12/2000 | Goeke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |

(Continued)

FOREIGN PATENT DOCUMENTS

| | | |
|---|---|---|
| GB | 2299166 | 9/1996 |
| GB | 9704444.0 | 3/1997 |

(Continued)

OTHER PUBLICATIONS

Bianchi, et al., "Large Amounts of Cell-free DNAS Are Present in Amniotic Fluid", Clin. Chem., 47(10) 1867-69 (2001).
Centre for Genomics Education, "Changes to Chromosome Structure—Translocations", The Australasian Genetics Resource Book, www.aenetics corn, pp. 1-5 (2007).
Chiu, et al., "Non-invasive prenatal diagnosis by single molecule counting technologies", Trends in Genomics,25(7):324-31 (2009).

(Continued)

*Primary Examiner* — Jerry Lin

(74) *Attorney, Agent, or Firm* — Mintz Levin Cohn Ferris Glovsky and Popeo, P.C.

(57) ABSTRACT

The present invention provides processes for calculating phased genomic sequences of the fetal genome using fetal DNA obtained from a maternal sample. The processes and systems of the present invention utilize novel technological and computational approaches to detect fetal genomic sequences and determine the phased heritable genomic sequences. The invention could be used, e.g., to identify in utero deleterious mutations carried by the parents and inherited by a fetus within a particular heritable genomic region.

20 Claims, 6 Drawing Sheets

(56) References Cited

U.S. PATENT DOCUMENTS

| | | |
|---|---|---|
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orland et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 8,318,430 B2 | 11/2012 | Chuu et al. |
| 10,289,800 B2 | 5/2019 | Stuelpnagel et al. |
| 2002/0045176 A1 | 4/2002 | Lo et al. |
| 2002/0132241 A1 | 9/2002 | Fan et al. |
| 2003/0003459 A1 | 1/2003 | Stahl |
| 2003/0044388 A1 | 3/2003 | Lo et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsuio et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0138809 A1 | 6/2008 | Kapur et al. |
| 2008/0206749 A1 | 8/2008 | Lo et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 6/2012 | Hixson |
| 2012/0191359 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0230258 A1 | 9/2012 | Miki |
| 2012/0237928 A1 | 9/2012 | Rava et al. |
| 2012/0264115 A1 | 10/2012 | Rava |

(56) References Cited

U.S. PATENT DOCUMENTS

| | | |
|---|---|---|
| 2012/0264121 A1 | 10/2012 | Rava et al. |
| 2012/0270739 A1 | 10/2012 | Rava et al. |
| 2013/0029852 A1 | 1/2013 | Rava |

FOREIGN PATENT DOCUMENTS

| | | |
|---|---|---|
| WO | WO87/006270 | 10/1987 |
| WO | WO90/06995 | 6/1990 |
| WO | WO99/47964 | 9/1999 |
| WO | WO2003/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 1/2010 |
| WO | WO2011/090557 | 1/2010 |
| WO | WO2011/090558 | 1/2010 |

OTHER PUBLICATIONS

Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology,34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action for U.S. Appl. No. 13/356,575, filed Jan. 23, 2012, inventor Oliphant (ARIA003CIP), entire document.
Office Action for U.S. Appl. No. 13/689,206, filed Nov. 29, 2012, inventor Oliphant (ARIA003CIPC), entire document.
Office Action for U.S. Appl. No. 13/356,133, filed Jan. 23, 2012, inventor Oliphant (ARIA003US), entire document.
Office Action for U.S. Appl. No. 13/013,732, filed Jun. 25, 2011, inventor Oliphant (ARIA004US), entire document.
Office Action for U.S. Appl. No. 13/405,839, filed Feb. 27, 2012, inventor Oliphant (ARIA005US), entire document.
Office Action for U.S. Appl. No. 13/407,978, filed Feb. 29, 2012, inventor Song (ARIA006US), entire document.
Office Action for U.S. Appl. No. 13/605,505, filed Sep. 6, 2012, inventor Struble (ARIA008US), entire document.
Office Action for U.S. Appl. No. 13/687,169, filed Nov. 28, 2012, inventor Sparks (ARIA009CON), entire document.
Office Action for U.S. Appl. No. 13/205,490, filed Aug. 8, 2011, inventor Sparks (ARIA009US), entire document.
Office Action for U.S. Appl. No. 13/687,025, filed Nov. 28, 2012, inventor Sparks (ARIA010CON), entire document.
Office Action for U.S. Appl. No. 13/687,025, filed Nov. 28, 2011, inventor Sparks (ARIA010CON), entire document.
Office Action for U.S. Appl. No. 13/205,570, filed Aug. 8, 2011, inventor Sparks (ARIA010US), entire document.
Office Action for U.S. Appl. No. 13/293,419, filed Nov. 10, 2011, Sparks (ARIA011US), entire document.
Office Action for U.S. Appl. No. 13/205,603, filed Aug. 8, 2011, inventor Sparks (ARIA012US), entire document.
Office Action for U.S. Appl. No. 13/274,309, filed Oct. 15, 2011, inventor Struble (ARIA013US), entire document.
Office Action for U.S. Appl. No. 13/245,133, filed Sep. 26, 2011, inventor Oliphant (ARIA014CIP), entire document.
Office Action for U.S. Appl. No. 13/689,417, filed Nov. 29, 2012, inventor Oliphant (ARIA016CIPC), entire document.
Office Action, filed Dec. 9, 2011, inventor Oliphant for U.S. Appl. No. 13/316,154 (ARIA016US), entire document.
Australian Patent Examination Report No. 1 dated Feb. 20, 2014 for 2011285512 (ARIA004AU), entire document.
Australian Patent Examination Report No. 1 dated Mar. 4, 2014 for 2011285518 (ARIA009AU), entire document.
Australian Patent Examination Report No. 1 dated Feb. 7, 2014 for 2011285477 (ARIA012AU), entire document.
EPO Examination Report dated Nov. 21, 2013 for App. No. 11745880.2 (ARIA004EP), entire document.
EPO Examination Report dated Nov. 21, 2013 for App. No. 11745881.1 (ARIA009EP), entire document.
EPO Examination Report dated Nov. 28, 2013 for App. No. 11745883.6 (ARIA012EP), entire document.
Search Report dated Sep. 12, 2013 for PCT/US 2012/026754 (ARIA005PCT), entire document.
Search Report dated Nov. 15, 2013 for PCT/US 201 3/51 31 0 (ARIA021 PCT), entire document.
Search Report dated May 14, 2013 for PCT/US 2014/17092 (ARIA023PCT), entire document.
Search Report dated Aug. 12, 2014 for PCT/US2013/75683 (ARIA022PCT), entire document.
Search Report for ARIA010PCT (PCT/US2011/046976), entire document.
Abadia-Molina, et al., "Immune phenotype and cytotoxic activity of lymploycytes from human term decidua against trophoblast", J. of Reproductive Immunology, n31:109-23 (1996).
Agostini, et al., "Circulating cell-free DNA: a promising marker of pathologic tumor response in rectal cancer patients receiving preoperative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks Gestation: Effect of Maternal and Fetal Factors, Fetal Dian Ther DOI:10.1159/000337373 (Pub'd online May 4, 2012).
Ashoor, et al., "Chromosome-selective sequencing of maternal plasma cell-free DNA for first-trimester detection of trisomy 21 and trisomy 18", Am. J. of Obstet. Gynecol., (2012), doi:10.1016/j.ajog. 2012.01.029.
Arnheim, et al., "Molecular evidence for genetic exchanges among ribosomal genes on nonhomologous chromosomes in man and apes", PNAS USA, 77(12)7323-27 (1980).
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).

(56) References Cited

OTHER PUBLICATIONS

Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neonatal human leucocytes expressing natural killer cell-associated antigen", Immunology and Cell Biology (71:535-42(1993).
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Natl Cancer Inst., 97(9):643-55 (2005).
Cicuttini and Boyd, "Hemopoietic and Lymphoid Progenitro Cells in Human Umbilical Cord Blood", Developmental Immunology, 4:1-11 (1994).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the maspin gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of tnsomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet.,15:441-45 (2007).
Conover, Practical Nonparametric Statistics, pp. 295-301 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. of Clinical Oncology, 12(3): 475-82 (1994).
Dear, et al., "A High-Resolution Metric HAPPY Map of Human Chromosome 14" Genmoics, 48 232-41 (1998).
Dennin, "DNA of Free and Complexed Origin in Human Plasma: Concentration and Length Distribution", Klin. Wochenschr., 57:451-56 (1979).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer",Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Enrich, et al., "Noninvasive detection of fetal trisomy 21 by sequencing of fetal DNA in maternal blood: a study in a clinical setting", Am J. Obstet Gynecol, 2011:204:205 el-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie, et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5): 1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).

(56) References Cited

OTHER PUBLICATIONS

Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874- (1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI10.1515/CCLM.2011.765) (2011).
Lun, et al., "Microfluidics Digital PCR Reveals a Higherthan Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Margulies, et al., "Genome sequencing in microfabricated high-density picolitre reactors", Nature, 437(15):376-80 and errata (2005).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine,2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Oei, et al., "Clusters of regulatory signals for RNA polymerase II transcription associated with Alu family repeats and CpG islands in human promoters", Genomics, 83:873-82 (2004).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Paolella, et al., "The Alu family repeat promoter has a tRNA-like bipartite structure", EMBO J., 2(5):691-96 (1983).
Papageorgiou, et al., "DNA methylation ratio permits noninvasive prenatal diagnosis of trisomy 21", Nat. Med., 17:510-13(2011).
Petersen, et al., "Down Syndrome Due to De Novo Robertsonian Translocation t(14q21q):DNA Polymorphism Analysis Suggests that the Origin of the Extra q21 is Maternal", Am. Ju. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).

(56) References Cited

OTHER PUBLICATIONS

Robbins, et al., Pathologic Basis of Disease 5th Ed., Chapter 23, pp. 1071-1088 (1994).
Ronaghi, et al., "A Sequencing Method Based on Real_Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Shendure, et al., "Accurate Multiplex Polony Sequencing of an Evolved Bacterial Genome", Science, 309:1728-32 (2005).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Simpson and Elias, "Isolating Fetal Cells from Maternal Blood", JAMA, 270(19):2357-61 (1993).
Simpson, et al., "Isolating Fetal Cells in Maternal Circulation for Prenatal Diagnosis", Prenatal Diagnosis, 14:1229-42 (1994).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.
Stroun, et al., "Neoplastic Characteristics of the DNA Found in the Plasma of Cancer Patients", Oncology, 46:318-322 (1989).
Stroun, et al., "Isolation and Characterization of DNA from the Plasma of Cancer Patients", Eur. J. Cancer Clin. Oncol., 23(6):707-12 (1987).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).
Tagle, et al., "An optimized Alu-PCR primer pair for human-specific amplification of YACs and somatic cells hybrids", Human Molecular Genetics, 1(2):121-22 (1992).
Tomilin, et al., "Mechanisms of Chromosome Destabilization in Human Cells", Soy. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684-91 (2011).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy numer variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
WU and WALLACE, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Enders, et al., "Fetal morbidity and mortality after acute human parvovirus B19 infection in pregnancy:prospective evaluation of 1018 cases", Prenatal Diagnosis, 24:513-18 (2004).
Smith, et al., "Quantitative phenotyping via deep barcode sequencing", Genome Res., 19:1836-42 (2009).

(56) References Cited

OTHER PUBLICATIONS

Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Search Report for ARIA012PCT (PCT/US2011/046981).
Search Report for ARIA016CIPPCT (PCT/US2012/21955).
Search Report for ARIA004PCT PCT/US2011/046935).
Search Report for ARIA005PCT (PCT/US2012/026754).
Search Report for ARIA016CIP2PCT (PCT/US2012/022261).
Search Report for ARIA009PCT (PCT/US2011/046963), entire document.
Search Report for ARIA015PCT (PCT/US2012/70177), entire document.
Office Action for U.S. Appl. No. 13/356,133 (ARIA003US, inventor A. Oliphant, filed Jan. 23, 2012), entire document.
Office Action for U.S. Appl. No. 13/356,575 (ARIA003CIP, inventor A. Oliphant, filed Jan. 23, 2012), entire document.
Office Action for U.S. Appl. No. 13/689,206 (ARIA003CIPC, inventor A. Oliphant, filed Nov. 39, 2012).
Final Office Action for U.S. Appl. No. 13/689,206 (ARIA003CIPC, inventor A. Oliphant, filed Nov. 39, 2012), entire document.
Office Action for U.S. Appl. No. 13/013,732 (ARIA004US, inventor A. Oliphant, filed Jun. 25, 2011).
Office Action for U.S. Appl. No. 13/013,732 (ARIA004US, inventor A. Oliphant, filed Jun. 25, 2011), entire document.
Office Action for U.S. Appl. No. 13/407,978 (ARIA006US, inventor K. Song, filed Feb. 29, 2012), entire document.
Office Action for U.S. Appl. No. 13/205,490 (ARIA009US, inventor A. Sparks, filed Aug. 8, 2011), entire document.
Office Action for U.S. Appl. No. 13/687,169 (ARIA009C, inventor A. Sparks, filed Nov. 28, 2012), entire document.
Office Action for U.S. Appl. No. 13/205,570 (ARIA010US, inventor A. Sparks, filed Aug. 8, 2011), entire document.
Office Action for U.S. Appl. No. 13/687,025 (ARIA010C, inventor A. Sparks, filed Nov. 28, 2012), entire document.
Office Action for U.S. Appl. No. 13/293,419 (ARIA011US, inventor A. Sparks, filed Nov. 10, 2011), entire document.
Office Action Received for U.S. Appl. No. 13/293,419 (ARIA011US, inventor A. Sparks, filed Nov. 10, 2011), entire document.
Final Office Action for U.S. Appl. No. 13/293,419 (ARIA011US, inventor A. Sparks, filed Nov. 10, 2011), entire document.
Advisory Action for U.S. Appl. No. 13/293,419 (ARIA011 US, inventor A. Sparks, filed Nov. 10, 2011), entire document.
Office Action for U.S. Appl. No. 13/245,133 (ARIA014CIP, inventor A. Oliphant, filed Sep. 26, 2011), entire document.
Office Action for U.S. Appl. No. 13/316,154 (ARIA016US, inventor A. Oliphant, filed Dec. 9, 2011), entire document.
Office Action for U.S. Appl. No. 13/338,963 (ARIA016CIP, inventor A. Oliphant, filed Dec. 28, 2011), entire document.
Office Action for U.S. Appl. No. 13/689,417 (ARIA016CIPC, inventor A. Oliphant, filed Nov. 29, 2012), entire document.
Chromosome 14 Map (Mar. 14, 1996). The Genethon Human Genetic Linkage Map, Collections, Supplements, *Nature*, 3 pages.
Mikhaylov, V.M. et al., (Jun. 1989). "Changes in the quantity and synthesis of DNA in the nuclei of large decidual cells of rats in the course of their differentiation," Tsitologiya (Cytology) 31(6):677-683.
Moreno and Gomella, (Nov. 1998). "Circulating Prostate Cancer Cells Detected by Reverse Transcription—Polymerase Chain Reaction (RT-PCR: What do they mean?", Cancer Control Journal, 5(6):507-512.
Mulcahy, H.E. et al. (Apr. 2000). "Plasma DNA K-ras Mutations in Patients with Gastrointestinal Malignancies," Annals New York Academy of Sciences, 906:25-28.

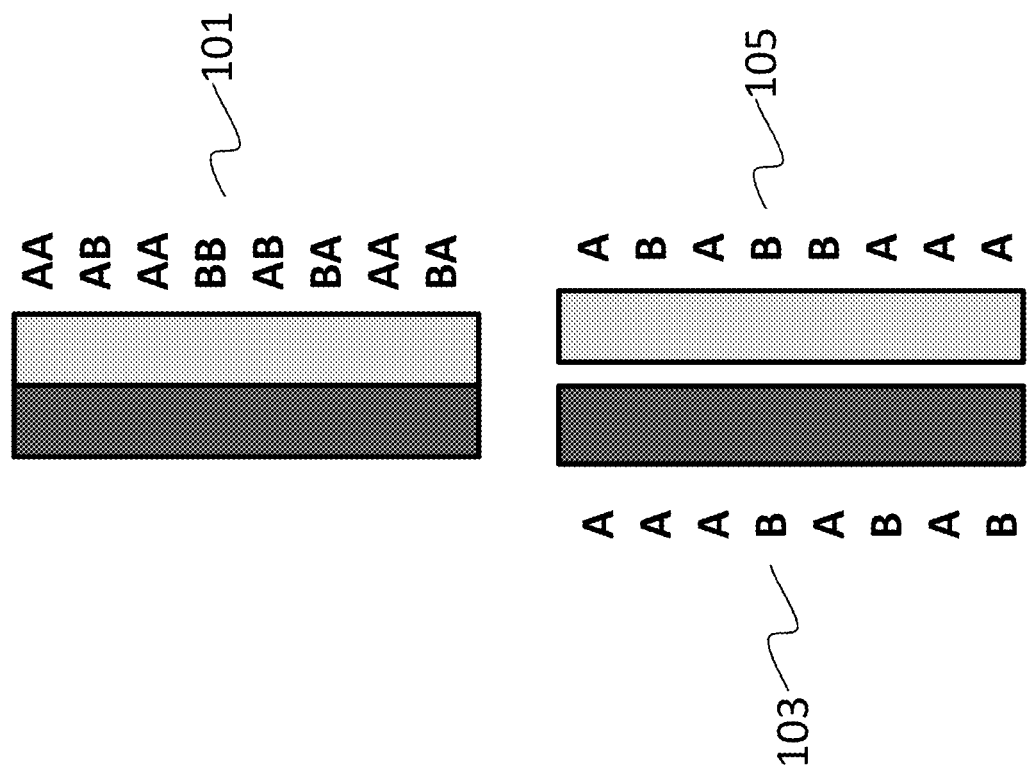

| SNP Analysis | | | |
|---|---|---|---|
| Maternal Allele | Paternal Allele | Fetal Allele | Status |
| Homozygous (AA) | Homozygous (AA) | Homozygous (AA) | Informative |
| Homozygous (AA) | Homozygous (BB) | Heterozygous (AB) | Informative |
| Homozygous (AA) | Heterozygous (AB) | Heterozygous (AB) | Informative |
| Homozygous (AA) | Heterozygous (AB) | Homozygous (AA) | Informative |
| Heterozygous (AB) | Homozygous (BB) | Heterozygous (AB) | Informative |
| Heterozygous (AB) | Homozygous (BB) | Homozygous (BB) | Informative |
| Heterozygous (AB) | Heterozygous (AB) | Homozygous (BB) | Informative |
| Heterozygous (AB) | Heterozygous (AB) | Heterozygous (AB) | Not Informative |

FIG. 2

PROCESSES FOR CALCULATING PHASED FETAL GENOMIC SEQUENCES

CROSS-REFERENCE TO RELATED APPLICATIONS

This application is a continuation application of U.S. patent application Ser. No. 13/898,239 (now issued U.S. Pat. No. 10,289,800), filed May 20, 2013, entitled "PROCESSES FOR CALCULATING PHASED FETAL GENOMIC SEQUENCES" which claims the benefit of U.S. Provisional Application Ser. No. 61/649,445, filed May 21, 2012, the contents of each are incorporated by reference herewith in their entirety.

FIELD OF THE INVENTION

The invention provides processes for calculating phased genomic information for a fetus using maternal samples including maternal blood, plasma and serum.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

An individual's genetic profile plays an important role in determining risk for disease and response to medical therapy. The development of technologies that facilitate rapid whole-genome sequencing will provide unprecedented power in the estimation of disease risk. Improvements in sequencing technology have enabled cost effective generation of whole genome sequences for individuals. By combining whole genome sequence information with family or pedigree information or with longer sequencing read technology, one may also now phase genomes. A phased genome will describe which variants are aggregated together within chromosomal regions for a particular individual. The interrogation of the entire phased genome provides superior sensitivity to linked genetic features and identification of recombination events.

It has been long recognized that certain sources of biological samples from a pregnant mammal (e.g., blood or plasma), contains DNA from both the mother and the fetus. This recognition has led to the use of maternal samples to identify, non-invasively to the fetus, fetal genetic characteristics, including qualitative (e.g., sex determination and RhD status) and quantitative (fetal copy number variations including trisomies) genetic detection of fetal sequences (for review see, e.g., Lo et al., October 2011). It has also been demonstrated by deep sequencing of the cell-free DNA in a maternal sample that sequences representative of the entire fetal genome is present in circulation. (Lo Y-M et al., Sci Transl Med. 2010 Dec. 8; 2(61):61ra91.) However, the percent fetal DNA is usually present in a low amount, usually 3-40%. Although deep, whole-genome sequencing of the fetal genome has been performed, with conventional technologies this approach is at present economically infeasible for widespread clinical or commercial use.

Thus, improved processes and systems for the identification of inherited alleles in a fetus from a maternal sample would be of great benefit in the art. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides processes for calculating phased genomic sequences of the fetal genome using fetal DNA obtained from a maternal sample. The processes and systems of the present invention utilize novel technological and computational approaches to detect fetal genomic sequences and determine the phased heritable genomic sequences. The invention could be used, e.g., to identify in utero deleterious mutations carried by the parents and inherited by a fetus within a particular heritable genomic region.

The processes of the invention provide methods for "phasing" the fetal DNA, i.e. determining the nucleic acids that are heritably linked within a single genomic region, e.g., a chromosome. The phased data from the fetal sequences can be used to determine whether the fetus is at risk for many diseases, disorders and/or predispositions based on the inheritance of one or more heritable genomic regions present in the fetal genome.

In one aspect, the processes and systems of the invention utilize chromosome-specific genomic sequence information from the mother and/or father, and preferably both the mother and father. In a preferred embodiment, the processes and systems utilize phased, whole-genome, chromosome-specific information of both the mother and father. This sequence information from the mother and father may be obtained through whole genome sequencing or via other methods, e.g., array hybridization followed by phasing of the sequence data from the mother and/or father. Such knowledge of the parental genomes can be used to determine which clinically or phenotypically significant alleles are inherited in the fetus within a heritable genomic region.

In one aspect, the invention provides a computer-implemented process for determining the phased composition in a fetal heritable genomic region, comprising the steps of: providing phased sequence information from at least one corresponding parental heritable genomic region; identifying five or more informative loci in the fetal DNA from a maternal sample corresponding to a heritable genomic region of interest; determining the paternal contribution of the heritable genomic region of interest based on the identified paternal contribution of the five or more informative loci; calculating the maternal contribution of the heritable genomic region based on the determined paternal contribution and the five or more informative loci; and predicting the likely phased composition of the phased fetal heritable genomic region based on the maternal and paternal contributions of the heritable genomic region.

In another aspect, the invention provides a computer-implemented process for determining the phased composition in a fetal heritable genomic region, comprising the steps of: providing phased sequence information from the maternal and paternal genome on at least one corresponding heritable genomic region; masking sequence information on loci that are indistinguishable between the maternal and paternal genome; providing empirical sequence information on five or more informative loci from a maternal sample corresponding to the heritable genomic region; calculating the predicted paternal contribution of the heritable genomic region to the fetus based on the empirically identified paternal sequences of the five or more informative loci; calculating the predicted maternal contribution of the heritable genomic region to the fetus based on the ratio of empirically identified sequences in the maternal sample; and providing a likelihood value of the fetal heritable genomic region contributed by the maternal and/or paternal source based on the predicted maternal and paternal contributions of the heritable genomic region to the fetus.

In yet another aspect, the invention provides a computer-implemented process to calculate a value of likelihood for a fetal heritable genomic region, comprising: providing maternal and paternal sequence information for a heritable genomic region; providing empirical sequence information from a heritable genomic region within a maternal sample, wherein the sequence information is obtained from the maternal sample using massively parallel sequencing; identifying at least five informative loci within the maternal and paternal heritable genomic region; calculating a value of the likelihood of the heritable genomic region inherited by the fetus from the father based on the informative loci and the empirical sequence information; identifying at least five loci which are maternally and paternally heterozygous; and calculating a value of the likelihood of the heritable genomic region inherited by the fetus from the mother based on value of the likelihood of the heritable genomic region inherited by the fetus from the father and the empirical sequence information on the loci which are maternally and paternally heterozygous.

In a preferred aspect of the invention, the fetal genetic variation within one or more heritable genomic regions can be imputed from a subset of parental informative loci within the heritable genomic regions. Thus, identifying certain alleles in the fetal genome can allow information of alleles that are not directly detected to be imputed from those that are detected. In this way, the heritable genomic regions in the fetus can be identified from a subset of informative loci, and preferably five or more informative loci, within the paternally-inherited and maternally-inherited heritable genomic regions.

In some aspects the maternal sample is a cell free maternal sample, and preferably maternal plasma or serum. In other aspects, the maternal sample comprises fetal cells.

In preferred aspects, the phased sequence information of parental genome is provided by sequencing, and more preferably whole genome sequencing. Preferably this is accomplished using long-read sequencing technologies that are more effective in providing phased information, or by combining short-read with long-read sequencing technologies. When combining sequencing technologies, the short-read coverage of the genome is preferably 20× or greater and the long-read sequencing coverage of the genome is preferably less than 5×. In other aspects, the phased allelic sequence information of the corresponding parental heritable genomic region is determined in part by pedigree analysis.

Generally, the allelic sequence information from the fetus comprises sequence information from at least twenty informative loci in the heritable genomic region, although as few as five informative loci can be used. In some aspects, the allelic sequence information from the fetus comprises sequence information on at least fifty informative loci in the heritable genomic region. In more specific aspects, the allelic sequence information from the fetus comprises sequence information on at least one hundred informative loci in the heritable genomic region.

In certain aspects, phasing of the fetal nucleic acids is performed for a sub-chromosomal unit. In other aspects, phasing of the fetal nucleic acids is performed for an entire chromosome. In yet other aspects, phasing of the fetal nucleic acids is performed for multiple fetal chromosomes. In still other preferred aspects, it is performed for the entire fetal genome.

In some aspects, the fetal genomes are analyzed using sequence determination of fetal sequences, and assembly of heritable regions is performed via comparison to one or more external reference sequences. In some aspects, significant variants are grouped by chromosome and haplotype association to determine which groups of variants are associated in a heritable region.

It is a feature of the invention that the source of the fetal DNA can be cell-free DNA obtained from maternal plasma or serum, and the processes of the invention identifies the fetal phasing in the background of the maternal DNA. The background maternal DNA contribution in the maternal sample can be "removed" from consideration either biochemically, through sensitive detection and comparison of the frequency of haplotypes present in the cell-free DNA, and/or via analytical analysis.

In some aspects of the invention, the processes utilize information on the fetal contribution of both the maternal genome and the paternal genome in the calculation of the phased fetal genomic regions.

In a preferred aspect, both maternal and paternal genomic information is used in the analysis of the fetal genome.

In other aspects, the association of significant variants in a fetal heritable region is determined by sequencing, and preferably massively parallel sequencing followed by allelic assembly.

DESCRIPTION OF THE FIGURES

FIG. 1 is a diagram illustrating the difference between identification of fetal alleles and phased allelic information.

FIG. 2 is a chart illustrating informative loci.

DETAILED DESCRIPTION OF THE INVENTION

Figure 3:
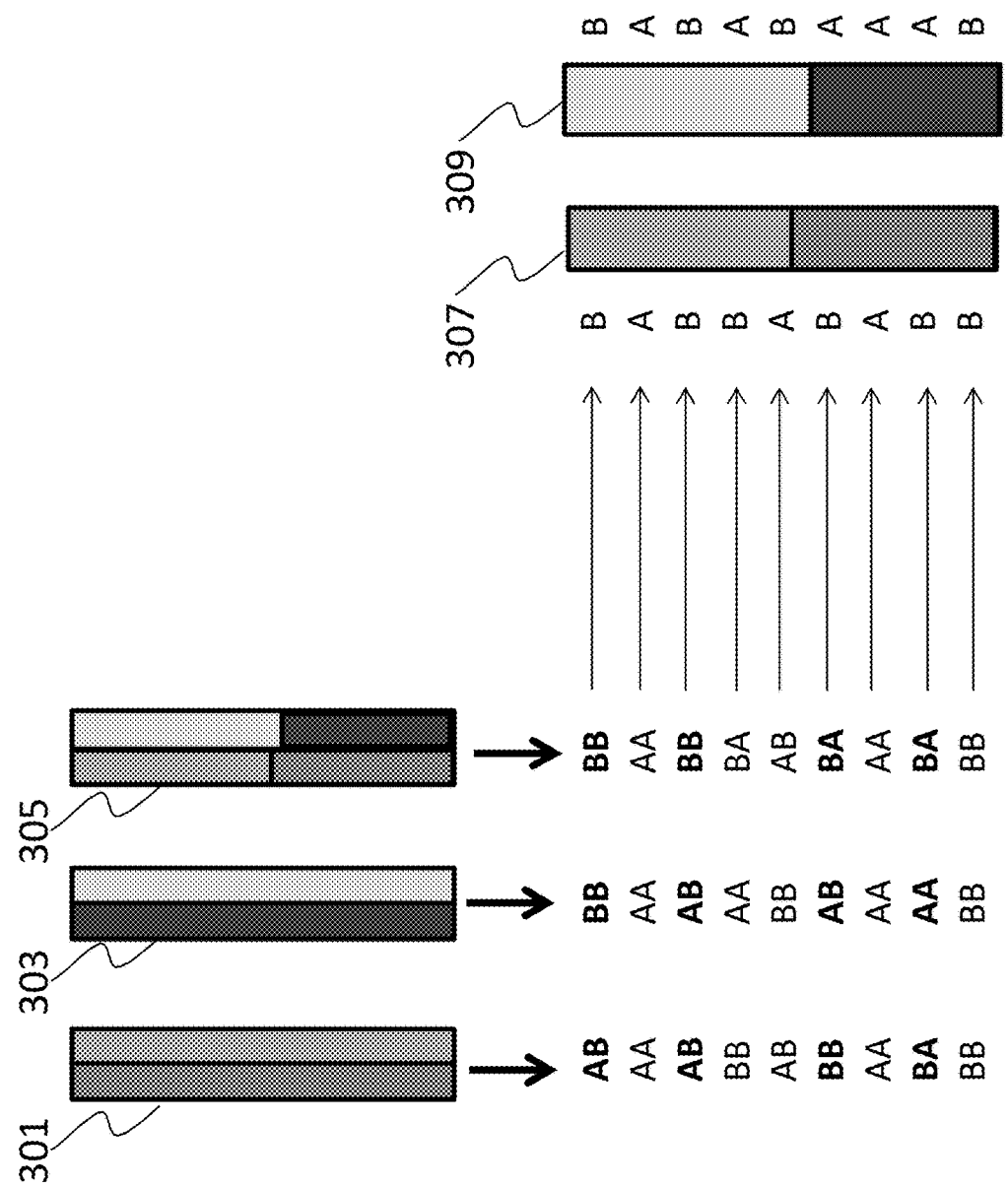
FIG. 3 is first illustration of fetal phased allelic chromosomes based on the maternal and paternal genotyping.

The processes described herein may employ, unless otherwise indicated, conventional techniques and descriptions of molecular biology (including recombinant techniques), genomics, biochemistry, and sequencing technology, which are within the skill of those who practice in the art. Such conventional techniques include hybridization and ligation of oligonucleotides, next generation sequencing, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory*

Manual Series (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, *"Oligonucleotide Synthesis: A Practical Approach"* IRL Press, London (1984); Nelson and Cox, *Lehninger, Principles of Biochemistry*, 3$^{rd}$ Ed., W. H. Freeman Pub., New York (2000); and Berg et al., *Biochemistry*, 5$^{th}$ Ed., W.H. Freeman Pub., New York (2002), all of which are herein incorporated by reference in their entirety for all purposes. Before the present compositions, research tools and processes are described, it is to be understood that this invention is not limited to the specific processes, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "an," and "the" include plural referents unless the context clearly dictates otherwise. Thus, for example, reference to "a nucleic acid region" refers to one, more than one, or mixtures of such regions, and reference to "an assay" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein, and in particular patent applications and issued patents, are incorporated by reference for the purpose of describing and disclosing various aspects, details and uses of the processes and systems that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication process performed in vitro as compared to the starting amount in a maternal sample.

The term "diagnostic tool" as used herein refers to any composition or assay of the invention used in combination as, for example, in a system in order to carry out a diagnostic test or assay on a patient sample.

The term "DNA contribution" refers to the percentage, proportion or measurement such as weight by volume of nucleic acid in a sample that is contributed by a source, such as the mother or a fetus.

The term "extrinsic factor" includes any information pertinent to the calculation of an odds ratio that is not empirically derived through detection of a maternal and fetal locus. Examples of such extrinsic factors include information related to maternal age, information related to gestational age, information related to previous pregnancies with an aneuploid fetus, previous serum screening results, ultrasound findings and the like. In preferred embodiments, the step of calculating and/or adjusting the computed odds ratio uses extrinsic factors related to both maternal age and gestational age.

The term "genetic feature" includes any feature within a genome that is identifiable using, e.g., techniques such as sequence determination or hybridization. Genetic features include, but are not limited to, single nucleotide polymorphisms, tandem single nucleotide polymorphisms, short tandem repeats, expansions (e.g., triplet code repeats), methylation patterns, and the like.

The term "heritable region" as used herein includes any larger portion of DNA from a single allele that can be elucidated using conventional phasing technologies available to those in the art. In certain preferred aspects, the heritable region is a chromosome. In most preferred aspects, multiple heritable regions are detected, and most preferably thus includes a subset of the chromosomes from a parent, and in a more preferred aspect all of the chromosomes inherited from a parent.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The terms "locus" and "loci" as used herein refer to a nucleic acid region of known location in a genome.

The term "informative locus" as used herein refers to a locus or pair of loci with one or more distinguishing regions useful in determining the phasing of a fetal heritable region.

The term "maternal sample" as used herein refers to any sample taken from a pregnant mammal which comprises a maternal source and a fetal source of nucleic acids (e.g., RNA or DNA).

The term "non-maternal" allele means an allele with a polymorphism and/or mutation that is found in a fetal allele (e.g., an allele with a de novo SNP or mutation) and/or a paternal allele, but which is not found in the maternal allele.

The term "phasing" as used herein refers to determination of genetic features which are located within a heritable region, e.g., the alleles that reside in a particular genomic region of a chromosome. For example, phasing can be performed on an entire chromosome to determine which genetic features will be heritably linked. Phasing thus provides the ability to distinguish which alleles belong to which chromosome, and to identify which alleles will be inherited together upon meiosis.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification processes may be used as an alternative to PCR.

The term "polymorphism" as used herein refers to any genetic characteristic in a locus that may be indicative of that particular locus, including but not limited to single nucleotide polymorphisms (SNPs), methylation differences, short tandem repeats (STRs), and the like.

The term "polymorphic locus" as used herein refers to a locus with two or more detectable alleles within a population. Generally, a polymorphic locus will have the most common allele less than 70%.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleotide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic, to be diagnostic or to be subject to regulatory approval; rather, the research tools of the invention are intended to facilitate research and aid in such development activities, including any activities performed with the intention to produce information to support a regulatory submission.

The term "selected nucleic acid region" as used herein refers to a nucleic acid region corresponding to a genomic region on an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the processing systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The terms "sequencing", "sequence determination" and the like as used herein refers generally to any and all biochemical processes that may be used to determine the order of nucleotide bases in a nucleic acid.

The term "specifically binds", "specific binding" and the like as used herein, refers to one or more molecules (e.g., a nucleic acid probe or primer, antibody, etc.) that bind to another molecule, resulting in the generation of a statistically significant positive signal under designated assay conditions. Typically the interaction will subsequently result in a detectable signal that is at least twice the standard deviation of any signal generated as a result of undesired interactions (background).

The term "value of the likelihood" refers to any value achieved by directly calculating likelihood or any value that can be correlated to or otherwise indicative of a likelihood.

The term "value of the probability" refers to any value achieved by directly calculating probability or any value that can be correlated to or otherwise indicative of a probability.

The Invention in General

The present invention provides methods for identifying the particular alleles in a fetal genome using a subset of allelic information from the fetus using a maternal sample and a determination of the phased genomic data of the mother and/or father. Phased data provides information not just on the genotype of the parent (i.e., the two alleles that are inherited for a particular genomic region), but also the organization of the genetic information (e.g., the haplotypes that are linked on a particular chromosome).

As a parent generally passes one of the two copies of each chromosome on to their offspring, the genes received by a child are typically heritably linked since they are located on the same chromosome. Knowledge of the phased genomic information of the parents allows a subset of alleles to be samples in the fetal genome to identify the likelihood that a fetus has inherited a particular chromosome from the mother and/or father.

The fetal genotypes are determined from a maternal sample, preferably cell-free DNA from a maternal blood sample. In one example, one determines the fetal genotype where the mother is homozygous and the fetus is heterozygous. In those instances, one identifies the "minor" allele. In another example, one determines the fetal genotype where the mother is heterozygous and the fetus is homozygous. This may be done by first genotyping the mother from a pure cellular sample and then comparing that genotype to that of the genotype from the maternal sample to observe a shift in the expected counts.

In one example, the maternal sample is genotyped at more than 5,000 locations in all chromosomes. In another example the sample is genotyped at more than 10,000 locations in all chromosomes. In another example, the sample is genotyped at more than 20,000 locations in all chromosomes. In another example, the sample is genotyped at more than 50,000 locations in all chromosomes. In another example, the sample is genotyped at more than 100,000 locations in all chromosomes.

The genotyping may be done with many different assays and detection platforms. With respect to preferred genotyping assays, one that facilitates high multiplexing is desirable.

In a preferred aspect, the maternal and fetal DNA is interrogated using sequence determination of universally amplified sequences. In certain aspects, this utilizes one of the following combined selective and universal amplification techniques: (1) LDR coupled to PCR; (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping Ronaghi et al., U.S. Pat. No. 7,622,281 describes amplification techniques for labeling and amplifying a nucleic acid using an adapter comprising a unique primer and a barcode.

In addition to the various amplification techniques, numerous methods of sequence determination are compatible with the processes and systems of the inventions. Preferably, such methods include "next generation" methods of sequencing. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Alternatively, nucleic acid regions of interest can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual ($2^{nd}$ Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623 each of which are incorporated herein by reference The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Patent application 60/364,731 and in PCT Application PCT/US99/06097 (published as WO99/47964), each of which also is hereby incorporated by reference in its entirety for all purposes.

Multiplexed PCR and array-based pull-outs are alternative options. With respect to detection platforms, the most preferred option is high-throughput DNA sequencing such as with Illumina, Complete Genomics and Ion Torrent. Array and qPCR read-outs are also possibilities. After the fetal genotypes have been determined, one compares those fetal genotypes to the phased parental genotypes. By using the haplotype information, one can identify alleles that would have been inherited together, thus identifying which chromosome or portions of chromosomes have been inherited. Once one has identified which chromosome or portions of chromosome have been inherited, one can then impute the fetal sequence. In the case where portions of chromosomes have been inherited, the sequence information between those portions is indeterminate. The amount of indeterminate sequence information is highly dependent upon the number of genotypes determined. Increasing the number of genotypes decreases the amount of indeterminate sequence information as one can determine with more certainty where the recombination site occurred. After the imputation of the fetal sequence, one may determine which clinically or phenotypically significant variants the fetus has inherited from each parent. It is important to note that one does not actually have to determine the fetal variant of clinical significance directly in the maternal sample. This can be done by imputing the variant from knowing the inheritance of other variants.

The processes and systems of the present invention utilize sequence information from heritable regions of the maternal and paternal genome to "phase" the fetal DNA obtained from a maternal source to obtain haplotype information for the heritable region of DNA. The parental genotypes for the heritable regions are determined using sequencing, and the linked alleles are identified through the sequencing process. As the fetal DNA may be available in the maternal sample as shorter regions (e.g., cell free DNA fragments), phasing of the fetal DNA may be more cost-effective than deep sequencing and assembly of the fetal genome.

Sequence information may be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

In some aspects, the fetal haplotypes are inferred by haplotype resolution or haplotype phasing techniques. These methods work by applying the observation that certain haplotypes are common in certain genomic regions. Therefore, given a set of possible haplotype resolutions, these methods choose those that use fewer different haplotypes overall.

In specific aspects, combinatorial approaches (e.g., parsimony) are used for haplotype phasing. In brief, haplotypes for an individual are selected among competing possible haplotypes and the one that offers the simplest explanation of the data derived from the fetal DNA is used to identify the most likely haplotypes for a heritable region.

In other specific aspects, likelihood functions are used. For example, haplotype phasing can be determined based on models and assumptions such as those that utilize genetic equilibrium (e.g., the Hardy-Weinberg principle). In the simplest case of a single locus with two alleles: the dominant allele is denoted A and the recessive a and their frequencies are denoted by p and q; freq(A)=p; freq(a)=q; p+q=1. If the population is in equilibrium, then we will have freq(AA)=$p^2$ for the AA homozygotes in the population, freq(aa)=$q^2$ for the aa homozygotes, and freq(Aa)=2pq for the heterozygotes.

Other aspects employ retrospective models of population genetics, e.g., the coalescent theory model. Each of these models can be combined with optimization algorithms such as expectation-maximization algorithm (EM), Markov chain Monte Carlo (MCMC), or hidden Markov models (HMM).

An example is in the case of cystic fibrosis (CF) testing. By sequencing, one would know that perhaps one or more of the parents are a CF carrier. The parents would like to know whether the fetus has inherited one allele, in which case it may be a CF carrier, or whether the fetus has inherited two alleles, in which case it may be symptomatic for CF. By genotyping informative loci close to the CF gene in the maternal sample, one may determine which chromosomes were inherited by the fetus and thus which CF alleles the fetus inherited from each parent, determining the CF status of the fetus.

Current approaches for full-scale genomic phasing require too much sequencing to be cost-effective. The processes of the invention using phasing based on fetal DNA fragments would greatly reduce the amount of sequencing necessary to determine the fetal genome in utero.

Techniques for Phasing the Fetal Genome

There are many ways to phase a mammalian genome, including long-range sequencing (>1000 bp) to identify overlapping haplotype information, sequencing or genotyping of predecessors or descendants to determine which alleles were inherited together, and imputation by population-based haplotype information.

For the present invention, information from one or both parents makes it possible to phase the fetal genome (for the vast majority of SNP calls) using a maternal sample. The processes of the invention rely on the fact that for most situations, the alleles inherited from the maternal and/or paternal genome can be provided, and these can be used not only to identify the value of likelihood of a specific chromosome being inherited by the fetus, but also identification of recombination events and the genomic.

For example, as illustrated in FIG. 1, if at a particular position, a fetal genotype call is AB (101), the paternal genotype is AA, and the maternal genotype is BB, the fetal A allele must have come from the father, and the fetal B allele must have come from the mother. Such alleles where fetal phase can be determined are considered informative. The cumulative data can be processed to determine a value of likelihood of a particular chromosome being inherited by the fetus. The A allele from the father is associated with a certain paternally-inherited fetal chromosome 103 while the B allele is associated with a certain maternally-inherited fetal chromosome 105. FIG. 2 provides examples of informative alleles based on maternal, paternal and fetal genotype that may be used in the processes of the invention.

FIG. 3 illustrates the utility of informative loci in determining the allelic make-up, and therefore phasing, of a fetal chromosome. The ability to test a limited number of allelic variants to infer all of the other alleles inherited by the fetus is a central concept of the invention. Thus, by determining the inheritance of the alleles shown in bold, the processes of the invention allow an imputation of the entire allelic makeup of the parentally-inherited chromosomes. Data on the alleles of a maternal phased chromosome 301 and a paternal phased chromosome 303 are provided, and the linked haplotype data from these chromosomes used to identify the phasing of the corresponding inherited fetal chromosomes 305. In this particular illustration, the fetal chromosomes each have a recombination event resulting in individual inherited chromosomes having alleles inherited from both paternal and maternal chromosomes.

The informative loci from the maternal and paternal genome allow both identification of the likely chromosomes inherited and the identification of the recombination event. The resulting data can be used to determine a value of likelihood that the inherited fetal chromosomes comprise specific linked alleles in view of the recombination events. Using the maternal and paternal phased genomic information, the likely inherited paternally-derived chromosome 307 and the maternally-derived chromosome 309 inherited by the fetus can be calculated using parental data.

Figure 4:
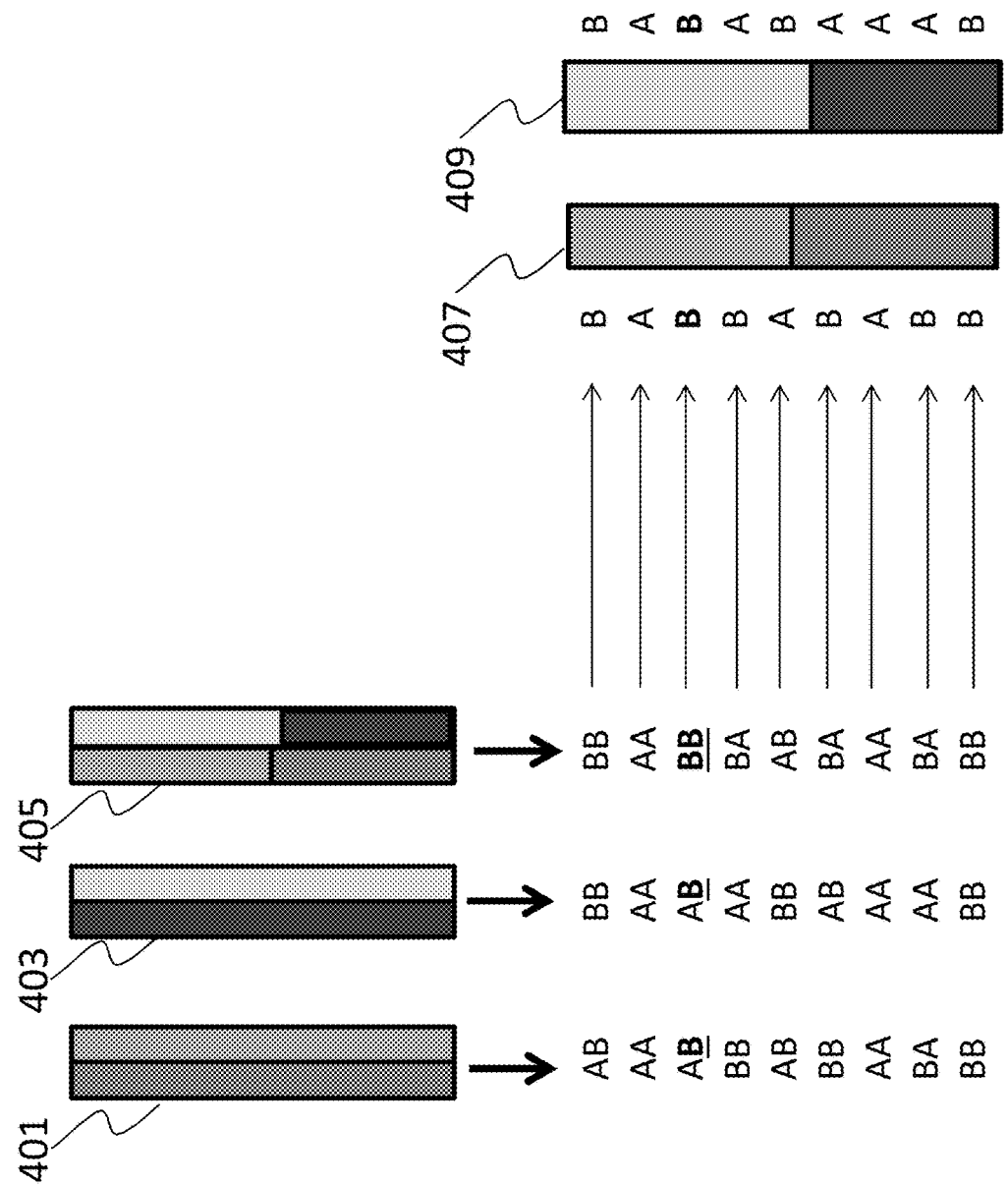
FIG. 4 is a second illustration of fetal phased allelic chromosomes based on the maternal and paternal genotyping.

FIG. 4 demonstrates the instance in which heterozygosity between maternal and paternal alleles can be informative. For example, if both parents have the genotype AB, and the fetus has the genotype BB, then both parents must have contributed the B genotype to the fetus.

Figure 5:
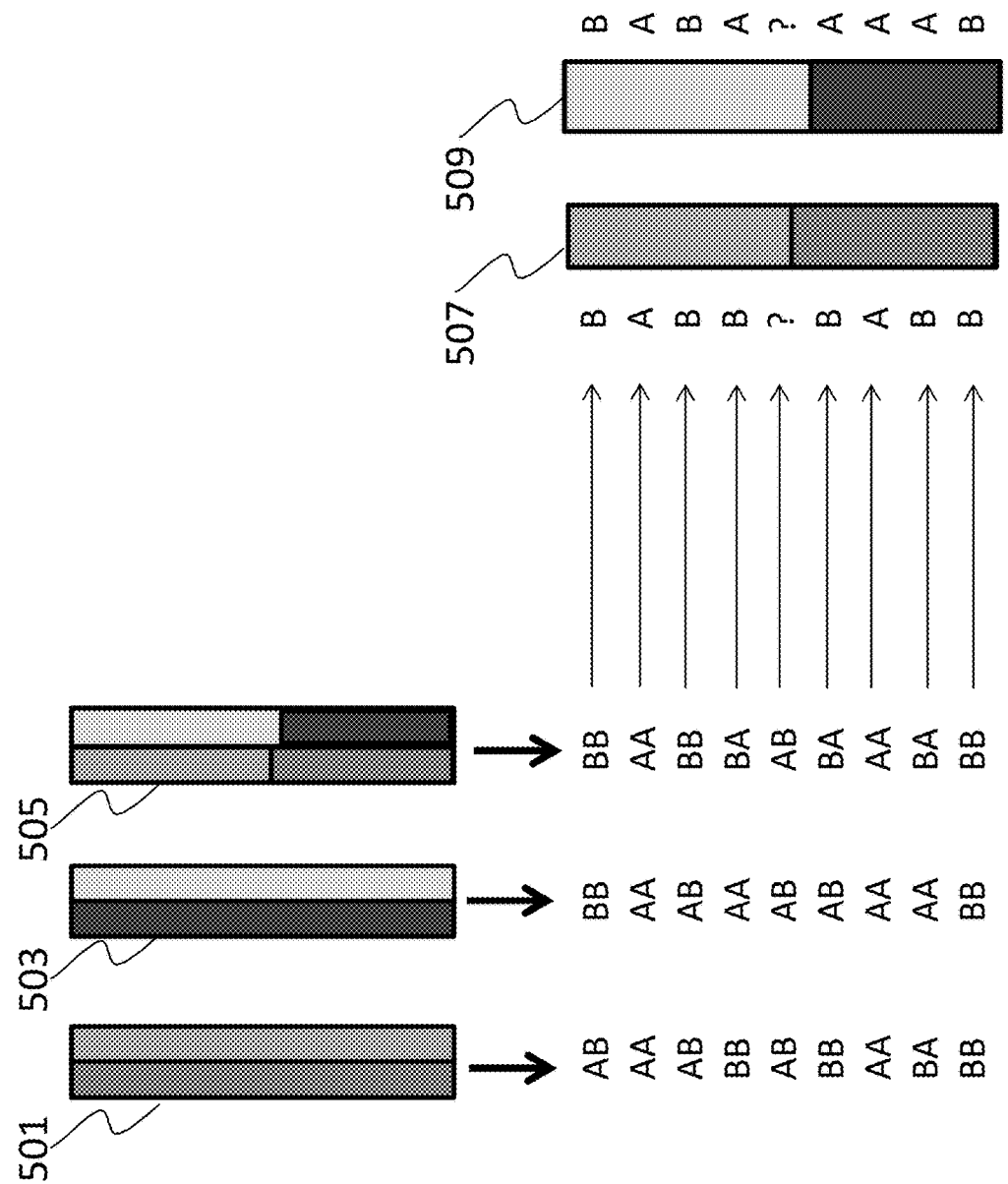
FIG. 5 is a third illustration of fetal phased allelic chromosomes based on the maternal and paternal genotyping.

In other implementations, such as that illustrated in FIG. 5, the phasing of the fetal DNA can be only partially determined based on the allelic data of a maternal phased chromosome 501 and a paternal phased chromosome 503. This data can be used to identify the phasing of the corresponding inherited fetal chromosomes 505. As in FIG. 3, the fetal chromosome has a recombination event in the DNA inherited from both the paternal and the maternal genome. The linked allelic information in FIG. 5, however, is ambiguous regarding the exact location of the recombination event due to heterozygosity at the maternal and paternal alleles at the site of recombination, so a value of likelihood for the fetal chromosomes can be determined on opposite sides of the recombination event but only as provided based on the available informative loci.

As the distinct position of the recombination event is unclear, a value of probability can be calculated given different markers and the value of likelihood that a recombination event may have occurred in a specific region of the chromosome. Using the maternal and paternal phased genomic information, the paternally-inherited fetal chromosome 507 and the maternally-inherited fetal chromosome 509 can be calculated but more information needs to be obtained in the recombination region to determine the allelic composition of the region.

In a preferred aspect, the processes of the invention utilizes paternal genomic information, maternal genomic information, and empirically-derived data from a maternal sample that comprises both maternal (the "major source") and fetal ("the minor source") DNA. The computational process provides a removal of all paternal and maternal genomic data which is the same across parental alleles, i.e., in which all homozygous loci that are the same between the mother and father are removed from the data set. Next, loci that are informative for the paternal allele in the fetus (i.e., "minor source informative") are determined, and alleles that are specific to the paternal source are identified. This can be calculated using the empirically-derived data from the maternal sample, using counts determined from the nucleic acids present representative of each allele present in the maternal sample. One example of this is the use of a binomial equation such as: Bin(A+B, X), where A is the empirically determined level of a first allele, B is the empirically determined level of a second allele, and X is a factor of the fetal contribution to the maternal sample. For example if the fetal contribution is approximately 10%, then X=0.5.

For the equation to have sufficient power, $X \geq \beta$, where $\beta$ is the minimum level of fetal contribution in a sample. As a general rule, $\beta$ should be 2 or greater, although this will also depend upon the number of informative loci used and the amount of parental information available to be used in the processes of the invention.

From this information, the paternal contribution can be inferred for multiple minor source haplotypes that are associated with the fetal chromosome inherited from the father.

Once the paternal alleles are identified for these regions, the maternal allele can be imputed based on the empirically-determined ratios of the nucleic acids representing the different alleles present in the maternal sample. If, for instance, the mother and father are both heterozygous for an allele, the maternally-inherited allele is the same as the paternally-inherited allele, and the fetal contribution X=0.5, then the identified nucleic acids representative of the allele in the maternal sample would be approximately 55/100 counts for that allele. If, however, maternally-inherited allele is the same as the paternally-inherited allele, and the fetal contribution X=0.5, then the identified nucleic acids representative of the allele in the maternal sample would be approximately 50/100 counts for that allele.

Empirical Determination of Fetal Contribution in a Maternal Sample

Determining which genetic loci are contributed to the fetus from paternal sources may in certain aspects utilize information on the fetal contribution in a maternal sample. The estimation of fetal DNA proportion in a maternal sample, provides information used to calculate statistically significant differences in dosages for alleles of interest, and thus collectively for heritable genomic regions of interest.

In certain aspects, determination of fetal polymorphisms requires targeted SNP and/or mutation analysis to identify the presence of fetal DNA in a maternal sample. In one preferred aspect, the percent fetal cell free DNA in a maternal sample can be quantified using multiplexed SNP detection based on knowledge of the maternal and/or paternal genotype. The selected polymorphic nucleic acid regions from the maternal sample (e.g., plasma) are amplified. In a preferred aspect, the amplification is universal; and in a preferred embodiment, the selected polymorphic nucleic acid regions are amplified in one reaction in one vessel. Each allele of the selected polymorphic nucleic acid regions is determined and quantified. In a preferred aspect, high throughput sequencing is used for such determination and quantification.

Identification of informative loci is accomplished by observing a high frequency of one allele (>80%) and a low frequency (<20% and >0.15%) of the other allele for a particular selected nucleic acid region. The use of multiple loci is particularly advantageous as it reduces the amount of variation in the measurement of the abundance of the alleles between loci. All or a subset of the loci that meet this requirement can used to determine fetal contribution through statistical analysis. In one aspect, fetal contribution is determined by summing the low frequency alleles from two or more loci together, dividing by the sum of the low and high frequency alleles and multiplying by two.

In one aspect, data from selected nucleic acid regions may be excluded if the data from the region appears to be an outlier due to experimental error or from idiopathic genetic bias within a particular sample. In another aspect, selected data from certain nucleic acid regions may undergo statistical or mathematical adjustment such as normalization, standardization, clustering, or transformation prior to summation or averaging. In another aspect, data from selected nucleic acid regions may undergo both normalization and data experimental error exclusion prior to summation or averaging.

In a preferred aspect, data from 12 or more nucleic acid regions or loci are used for the analysis. In another preferred aspect, data from 24 or more nucleic acid regions or loci are used for the analysis. In another preferred aspect, data from 48 or more loci are used for the analysis. In another aspect, one or more indices are used to identify the sample, the locus, the allele or the identification of the nucleic acid. Such indices are as is described in co-pending applications U.S. Ser. Nos. 13/205,490 and 13/205,570 hereby incorporated herein by reference in their entirety.

In one preferred aspect, the percentage fetal contribution in a maternal sample is quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. Ser. Nos. 12/581,070, 12/581,083, 12/689,924, and 12/850,588. These references describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample and used to determine the fetal proportion of nucleic acids in the maternal sample.

Determination of Fetal DNA Content in a Maternal Sample Using Epigenetic Allelic Ratios Certain genes have been identified as having epigenetic differences between the fetus and the mother, and such genes are candidate loci for fetal DNA markers in a maternal sample. See, e.g., Chim, et al., PNAS USA, 102:14753-58 (2005). These loci, which are unmethylated in the fetus but are methylated in maternal blood cells, can be readily detected in maternal plasma. The comparison of methylated and unmethylated amplification products from a maternal sample can be used to quantify the percent fetal DNA contribution to the maternal sample by calculating the epigenetic allelic ratio for one or more of such sequences known to be differentially-methylated in fetal DNA as compared to maternal DNA.

To determine methylation status of nucleic acids in a maternal sample, the nucleic acids of the sample are subjected to bisulfite conversion. Conventional processes for such bisulphite conversion include, but are not limited to, use of commercially available kits such as the Methylamp™ DNA Modification Kit (Epigentek, Brooklyn, N.Y.). Allelic frequencies and ratios can be directly calculated and exported from the data to determine the percentage of fetal DNA in the maternal sample.

Human Reference Sequences

One of the challenges to interpretation of genome sequence data is the assembly and variant calling of sequence reads against the human reference genome. Although de novo assembly of genome sequences from raw sequence reads represents an alternative approach, computational limitations and the large amount of mapping information encoded in relatively invariant genomic regions make this an unattractive option presently. The National Center for Biotechnology Information (NCBI) human reference genome (Pruitt K D et al., Nucleic Acids Res. 2012 January; 40(Database issue):D130-5. Epub 2011 Nov. 24) is derived from DNA samples from a small number of anonymous donors and therefore represents a small sampling of the broad array of human genetic variation. For purposes of more diverse populations (or populations of specific descent) or more tailored genomes (individual genomes or cumulative reference of multiple genomes).

In some aspects of the invention, synthetic human reference sequences that are ethnically concordant with a pregnant subject and her family are used for the analysis of genomes from a nuclear family. Such reference sequences are described, e.g., in Dewey F E et al., PLoS Genet. 2011 September; 7(9):e1002280. Epub 2011 Sep. 15. The use of a major allele reference sequence results in improved genotype accuracy for variant loci. Recombination sites can be inferred to the lowest median resolution demonstrated to date (<1,000 base pairs).

Determination of the whole genome sequence of the mother and fetus, and preferably the mother, father and fetus allows multigenic risk for inherited diseases and disorders, and may also be useful in optimizing pharmaceutical intervention based on metabolism or predicted response to various drugs. These ethnicity-specific, family-based approaches to interpretation of genetic variation are emblematic of the next generation of genetic risk assessment using whole-genome sequencing.

Computer Implementation of the Processes of the Invention

Figure 6:
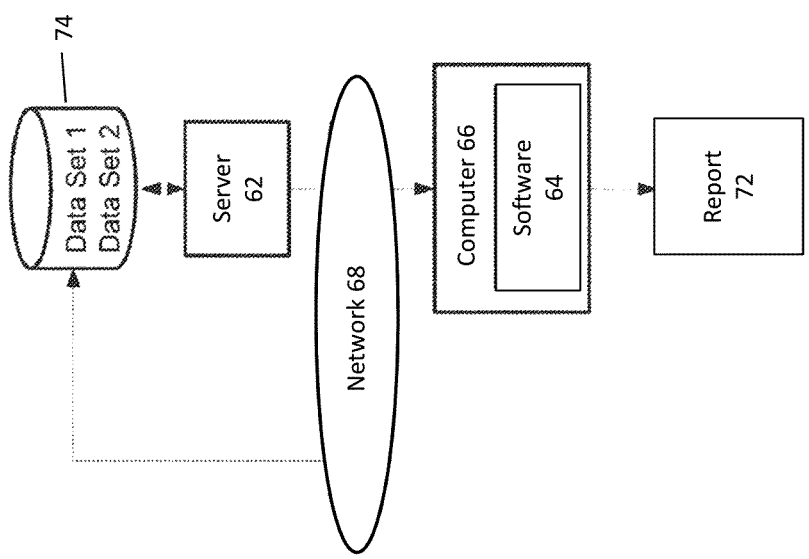
FIG. 6 is a block diagram illustrating an exemplary system environment.

FIG. 6 is a block diagram illustrating an exemplary system environment 60 in which the processes of the present invention may be implemented for calculating chromosome or loci dosage and fetal DNA contribution. The system 60 includes a server 62 and a computer 66. The computer 66 may be in communication with the server 62 through the same or different network 68.

According to the exemplary embodiment, the computer 66 executes a software component 64 that calculates fetal phased genomic information based on the provided data sets 74. In one embodiment, the computer 66 may comprise a personal computer, but the computer 66 may comprise any type of machine that includes at least one processor and memory.

The output of the software component 64 comprises a report 72 with a value of likelihood of inheritance of one or more heritable genomic regions. The report 72 may be paper that is printed out, or electronic, which may be displayed on a monitor and/or communicated electronically to users via e-mail, FTP, text messaging, posted on a server, and the like.

Although the process of the invention is shown as being implemented as software 64, it can also be implemented as a combination of hardware and software. In addition, the software 64 may be implemented as multiple components operating on the same or different computers.

Both the server 62 and the computer 66 may include hardware components of typical computing devices (not shown), including a processor, input devices (e.g., keyboard, pointing device, microphone for voice commands, buttons, touchscreen, etc.), and output devices (e.g., a display device, speakers, and the like). The server 62 and computer 66 may include computer-readable media, e.g., memory and storage devices (e.g., flash memory, hard drive, optical disk drive, magnetic disk drive, and the like) containing computer instructions that implement the functionality disclosed when executed by the processor. The server 62 and the computer 66 may further include wired or wireless network communication interfaces for communication.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed:

1. A computer-implemented process for determining the phased composition in a fetal heritable genomic region from a maternal sample comprising maternal DNA and fetal DNA, the process comprising the steps of:
   isolating cell-free nucleic acids from the maternal sample comprising the maternal DNA and the fetal DNA, wherein the cell-free nucleic acids comprise selected nucleic acid regions;
   interrogating the selected nucleic acid regions in the fetal heritable genomic region using oligonucleotides to amplify the selected nucleic acid regions, the oligonucleotides comprising universal amplification sequences;

applying the amplified selected nucleic acid regions to an array-based pull-out detection system to identify informative loci corresponding to a heritable genomic region of interest;

providing, to a computer processor, phased sequence information from a maternal genome and a paternal genome on at least one corresponding parental heritable genomic region;

masking, by the computer processor, sequence information on loci of the parental heritable genomic region that are indistinguishable between the maternal genome and the paternal genome;

providing, by the computer processor, empirical sequence information on five or more informative loci from the maternal sample corresponding to the heritable genomic region of interest;

calculating, by the computer processor, a predicted paternal contribution of the heritable genomic region of interest using the empirical sequence information of the five or more informative loci;

calculating, by the computer processor, a predicted maternal contribution of the heritable genomic region of interest using the empirical sequence information; and generating, by the computer processor, a likelihood value of the fetal heritable genomic region contributed by a maternal source and/or a paternal source using the predicted maternal contribution and the predicted paternal contribution of the heritable genomic region of interest.

2. The process of claim 1, wherein the maternal sample is maternal plasma or serum.

3. The process of claim 1, wherein the phased sequence information of the parental heritable genomic region is determined by sequencing of the maternal genome and the paternal genome.

4. The process of claim 1, wherein a fetal genetic variation within the fetal heritable genomic region is imputed from a subset of parental informative loci.

5. The process of claim 1, wherein the phased sequence information of the at least one corresponding parental heritable genomic region is determined by pedigree analysis.

6. The process of claim 1, wherein the phased sequence information from a fetal source comprises sequence information on at least twenty informative loci in the fetal heritable genomic region.

7. The process of claim 1, wherein the fetal heritable genomic region comprises a sub-chromosomal unit.

8. A computer-implemented process to calculate a value of likelihood for
a fetal heritable genomic region from a maternal sample comprising maternal DNA and fetal
DNA, the process, comprising:
isolating cell-free nucleic acids from the maternal sample comprising the maternal DNA and the fetal DNA, wherein the cell-free nucleic acids comprise selected nucleic acid regions;
interrogating the selected nucleic acid regions in the fetal heritable genomic region using oligonucleotides to amplify the selected nucleic acid regions, the oligonucleotides comprising universal amplification sequences;

applying the amplified selected nucleic acid regions to an array-based pull-out detection system to identify informative loci corresponding to a heritable genomic region of interest;

providing, to a computer processor, maternal sequence information and paternal sequence information for a parental heritable genomic region;

providing, by the computer processor, empirical sequence information from the heritable genomic region of interest, wherein the empirical sequence information is obtained from the maternal sample using massively parallel sequencing;

identifying, by the computer processor, at least five informative loci within the parental heritable genomic region;

calculating, by the computer processor, a value of the likelihood of the fetal heritable genomic region inherited by a paternal source using the at least five informative loci and the empirical sequence information;

identifying, by the computer processor, at least five loci that are maternally and paternally heterozygous;

calculating, by the computer processor, a value of the likelihood of the fetal heritable genomic region inherited by a maternal source using the value of the likelihood of the fetal heritable genomic region inherited by the paternal source and the empirical sequence information on the at least five loci that are maternally and paternally heterozygous.

9. The process of claim 8, wherein the maternal sample is a cell free maternal sample.

10. The process of claim 9, wherein the cell free maternal sample is maternal plasma or serum.

11. The process of claim 8, wherein the maternal sample comprises fetal cells.

12. The process of claim 8, wherein phased sequence information of the parental heritable genomic region is determined by sequencing of a maternal genome and a paternal genome.

13. The process of claim 8, wherein a fetal genetic variation within the fetal heritable genomic region is imputed from a subset of parental informative loci.

14. The process of claim 8, wherein phased sequence information of the parental heritable genomic region is determined by pedigree analysis.

15. The process of claim 8, wherein phased sequence information from a fetal source comprises sequence information on at least twenty informative loci in the fetal heritable genomic region.

16. The process of claim 8, wherein phased sequence information from a fetal source comprises sequence information on at least fifty informative loci in the fetal heritable genomic region.

17. The process of claim 8, wherein phased sequence information from a fetal source comprises sequence information on at least one hundred informative loci in the fetal heritable genomic region.

18. The process of claim 8, wherein the fetal heritable genomic region comprises a sub-chromosomal unit.

19. The process of claim 8, wherein the fetal heritable genomic region comprises an entire chromosome.

20. The process of claim 8, wherein the fetal heritable genomic region comprises the entire genome.

* * * * *